000
(12) United States Patent
Kawamata et al.

(10) Patent No.: US 10,352,870 B2
(45) Date of Patent: Jul. 16, 2019

(54) LED LIGHT SOURCE PROBE CARD TECHNOLOGY FOR TESTING CMOS IMAGE SCAN DEVICES

(71) Applicant: FormFactor, Inc., Livermore, CA (US)

(72) Inventors: Nobuhiro Kawamata, Tsukuba (JP); Toshihiro Kasai, Sagamihara (JP); Hiromitsu Sasanami, Yokohama (JP); Shigeki Mori, Ebina (JP)

(73) Assignee: FormFactor, Inc., Livermore, CA (US)

( * ) Notice: Subject to any disclaimer, the term of this patent is extended or adjusted under 35 U.S.C. 154(b) by 42 days.

(21) Appl. No.: 15/835,380

(22) Filed: Dec. 7, 2017

(65) Prior Publication Data

US 2018/0164223 A1 Jun. 14, 2018

Related U.S. Application Data

(60) Provisional application No. 62/432,548, filed on Dec. 9, 2016.

(51) Int. Cl.
*G01N 21/88* (2006.01)
*G01J 1/42* (2006.01)
(Continued)

(52) U.S. Cl.
CPC ........ *G01N 21/8806* (2013.01); *G01J 1/0418* (2013.01); *G01J 1/08* (2013.01); *G01J 1/32* (2013.01); *G01J 1/42* (2013.01); *G01N 21/88* (2013.01); *G01R 31/28* (2013.01); *G01R 31/2889* (2013.01); *G02B 27/0955* (2013.01); (Continued)

(58) Field of Classification Search
CPC ....... G01M 11/00; G01N 21/17; G01N 21/88; G01N 21/8806; G01J 1/08; G01J 1/32; G01J 1/42; G01J 1/0418; G01J 2001/4252; G01R 31/28; G01R 31/2889; G02B 27/0955; H04N 1/028; H04N 1/0288; H04N 1/02885

See application file for complete search history.

(56) References Cited

U.S. PATENT DOCUMENTS 6,625,558 B1 9/2003 Ausdall et al.
7,136,157 B2 11/2006 Gomm et al.
(Continued)

OTHER PUBLICATIONS

Hancock et al., "An Optical Source for Characterizing CMOS Imagers", 2004, Proc. SPIE 5529 pp. 140-149.

*Primary Examiner* — Jamil Ahmed
(74) *Attorney, Agent, or Firm* — Lumen Patent Firm

(57) ABSTRACT

Improved wafer-scale testing of optoelectronic devices, such as CMOS image scan devices, is provided. A probe card includes an LED light source corresponding to each device under test in the wafer. The LED light sources provide light from a phosphor illuminated by the LED. A pinhole and lens arrangement is used to collimate the light provided to the devices under test. Uniformity of illumination can be provided by closed loop control of the LED light sources using internal optical signals as feedback signals, in combination with calibration data relating the optical signal values to emitted optical intensity. Uniformity of illumination can be further improved by providing a neutral density filter for each LED light source to improve uniformity from one source to another and/or to improve uniformity of the radiation pattern from each LED light source.

12 Claims, 6 Drawing Sheets

(51) Int. Cl.
*G02B 27/09* (2006.01)
*G01R 31/28* (2006.01)
*H04N 1/028* (2006.01)
*G01J 1/08* (2006.01)
*G01J 1/32* (2006.01)
*G01J 1/04* (2006.01)

(52) U.S. Cl.
CPC ........... *H04N 1/028* (2013.01); *H04N 1/0288* (2013.01); *H04N 1/02885* (2013.01); *G01J 2001/4252* (2013.01)

(56) References Cited

U.S. PATENT DOCUMENTS

| 7,864,381 | B2 | 1/2011 | Scott |
| 2011/0291564 | A1 | 12/2011 | Huang |
| 2016/0161294 | A1* | 6/2016 | Ip .............................. G01D 5/34 250/578.1 |

* cited by examiner

| | | | |
|---|---|---|---|
| 481.250 | 515.461 | 517.610 | 489.189 |
| 506.858 | 539.214 | 543.078 | 507.767 |
| 515.596 | 540.774 | 539.932 | 528.548 |
| 516.429 | 551.298 | 552.416 | 527.342 |
| 506.770 | 534.019 | 533.499 | NA |
| 505.786 | 555.190 | 543.808 | 512.950 |
| 496.279 | 526.900 | 530.242 | 506.960 |
| 463.187 | NA | 495.725 | NA |

FIG. 4A

| | | | |
|---|---|---|---|
| 550.829 | 547.876 | 550.244 | 552.087 |
| 549.320 | 551.410 | 552.220 | 546.742 |
| 549.200 | 552.883 | 547.279 | 549.181 |
| 552.182 | 546.430 | 547.173 | 549.575 |
| 547.081 | 549.316 | 551.191 | 552.362 |
| 550.399 | 551.122 | 548.105 | 549.687 |
| 551.835 | 550.963 | 548.861 | 546.749 |
| 549.264 | 548.041 | 552.307 | 548.851 |

FIG. 4B

| | | | |
|---|---|---|---|
| 451.230 | 489.424 | 490.807 | 451.203 |
| 491.039 | 536.851 | 521.555 | 476.657 |
| 498.557 | 551.422 | 543.942 | 501.097 |
| 505.300 | 551.256 | 550.315 | 500.009 |
| 507.687 | 548.114 | 541.678 | 493.767 |
| 496.213 | 535.792 | 538.548 | 496.388 |
| 489.515 | 543.533 | 544.201 | 479.103 |
| 455.371 | 471.982 | 483.247 | 455.782 |

FIG. 5A

| | | | |
|---|---|---|---|
| 558.173 | 555.783 | 557.201 | 555.524 |
| 559.492 | 560.356 | 558.371 | 561.663 |
| 560.904 | 562.156 | 554.423 | 558.185 |
| 558.147 | 556.436 | 560.664 | 559.583 |
| 558.451 | 559.588 | 560.001 | 562.049 |
| 564.045 | 558.246 | 560.032 | 555.906 |
| 559.361 | 554.884 | 560.814 | 562.318 |
| 560.378 | 562.035 | 561.588 | 558.054 |

FIG. 5B

LED LIGHT SOURCE PROBE CARD TECHNOLOGY FOR TESTING CMOS IMAGE SCAN DEVICES

CROSS REFERENCE TO RELATED APPLICATIONS

This application claims the benefit of U.S. provisional patent application 62/432,548, filed on Dec. 9, 2016, and hereby incorporated by reference in its entirety.

FIELD OF THE INVENTION

This invention relates to probing and testing of optoelectronic devices, especially CMOS image scan (CIS) devices.

BACKGROUND

Conventional testing of CMOS (complementary metal-oxide-silicon) image scan devices makes use of a halogen lamp to provide light for testing. This arrangement has significant disadvantages, including large size, significant required maintenance and difficulty in reconfiguring test setups. These problems become especially acute in the context of wafer-scale device testing, where a light source having a diameter as high as 300 mm may be required. Accordingly, it would be an advance in the art to provide an improved light source/probe card for testing optoelectronic devices.

SUMMARY

We provide a solution to the above-described problems based on the use of light emitting diodes (LEDs) as the light source for CIS device testing. The basic architecture is an LED array having one LED source per CIS device chip being tested. Arrays of LEDs are used because such testing is typically done wafer-scale, as opposed to being performed individually for single devices. The LEDs illuminate a phosphor which provides the light used for testing. An aperture+lens arrangement is used to provide telecentric light. In some embodiments, the aperture can be used as part of the cooling arrangement for the LEDs.

Uniformity filters can be used to improve illumination uniformity within a chip and/or from one chip to the next. Such filters can be regarded as pixelated neutral density filters. Operation under closed loop control can be used to correct for device to device variation among the LEDs. In one example, such control makes use of two calibration tables, one for high illuminance (i.e., over 100 lx) and low illuminance (i.e., 100 lx or less). Another feature of the feedback control in one example is the use of two photodetectors, one photodetector having a neutral density filter on it, and the other photodetector not having a neutral density filter on it. Feedback control of LED intensity can make use of two feedback paths: 1) LED to photodetector and 2) LED to phosphor to photodetector. Feedback control can also be done with a single photodetector in the LED light source module, either with or without a neutral density filter on the photodetector.

BRIEF DESCRIPTION OF THE DRAWINGS

FIGS. 4A-B show first exemplary experimental results for array uniformity.
FIGS. 5A-B show second exemplary experimental results for array uniformity.

DETAILED DESCRIPTION

Figure 1A:
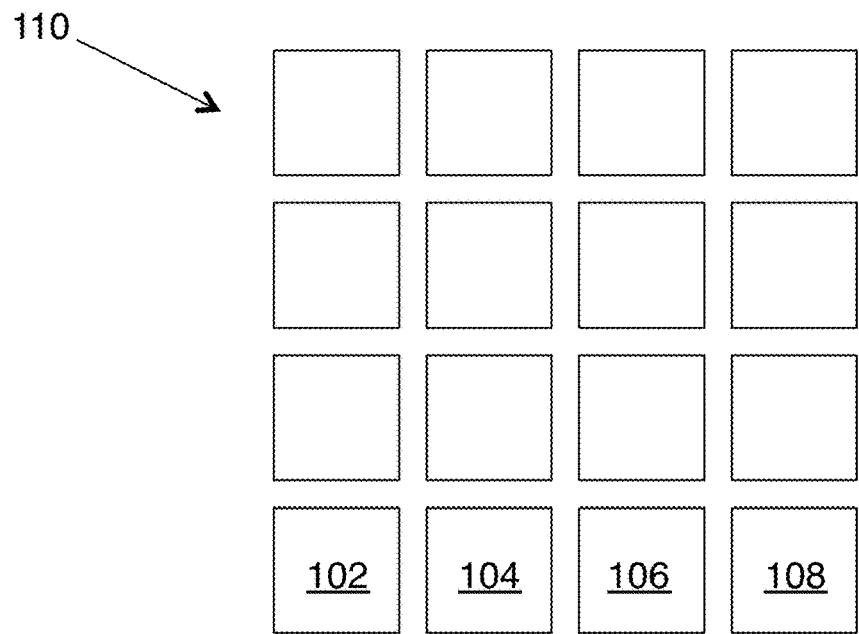
FIGS. 1A-B show an embodiment of the invention.
Figure 1B:
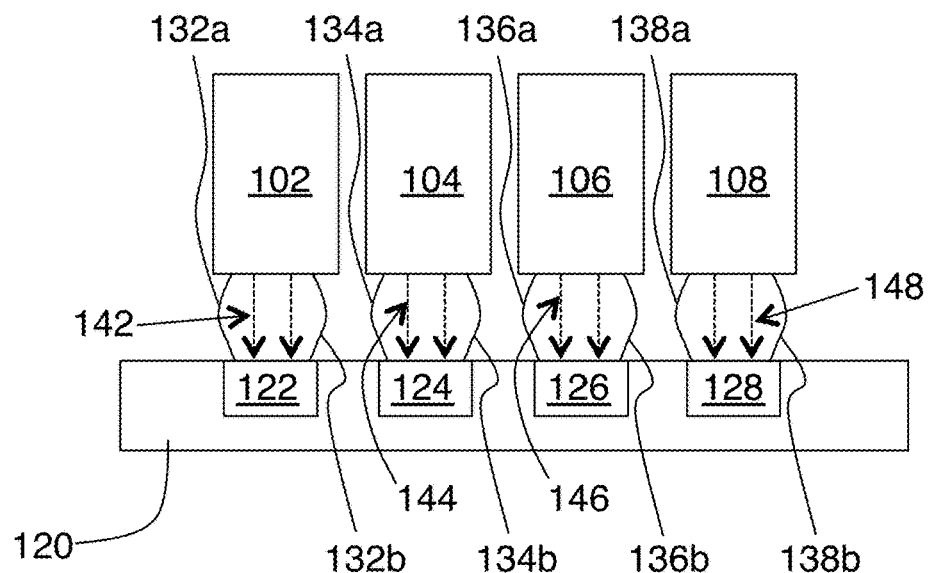

FIGS. 1A-B show an exemplary embodiment of the invention. Here FIG. 1A is a top view and FIG. 1B is a corresponding side view of apparatus for testing an array of light-sensitive electronic devices. FIG. 1A shows an array of LED (light emitting diode) light sources 110, four of which are referenced as 102, 104, 106, and 108. The array of sources need not be square as shown on FIG. 1A. Another possible variation is that gaps may be placed between the LED light sources so that the arrangement is not contiguous.

As shown in the side view of FIG. 1B, array 110 is configured to have an LED light source corresponding to each of the electronic devices under test. In this example, sources 102, 104, 106, 108 correspond to devices under test 122, 124, 126, 128, respectively. More specifically, sources 102, 104, 106, 108 provide output light 142, 144, 146, 148 to devices under test 122, 124, 126, 128, respectively. Here devices under test 122, 124, 126, 128 are schematically shown as being disposed in substrate 120, which would be the case for wafer scale testing.

An important advantage of the present approach is that the small size of the LED light sources simplifies integration of optical illumination and electrical probing to provide a true optoelectronic probe card for testing optoelectronic imaging devices. In the example of FIGS. 1A-B, this preferred feature is shown by electrical probes 132a,b, 134a,b, 136a,b, 138a,b which make electrical contact to electrical terminals of devices under test 122, 124, 126, 128, respectively. For ease of illustration, two electrical probes per device under test are shown, but in practice any number of electrical probes can be used per device under test.

Figure 2:
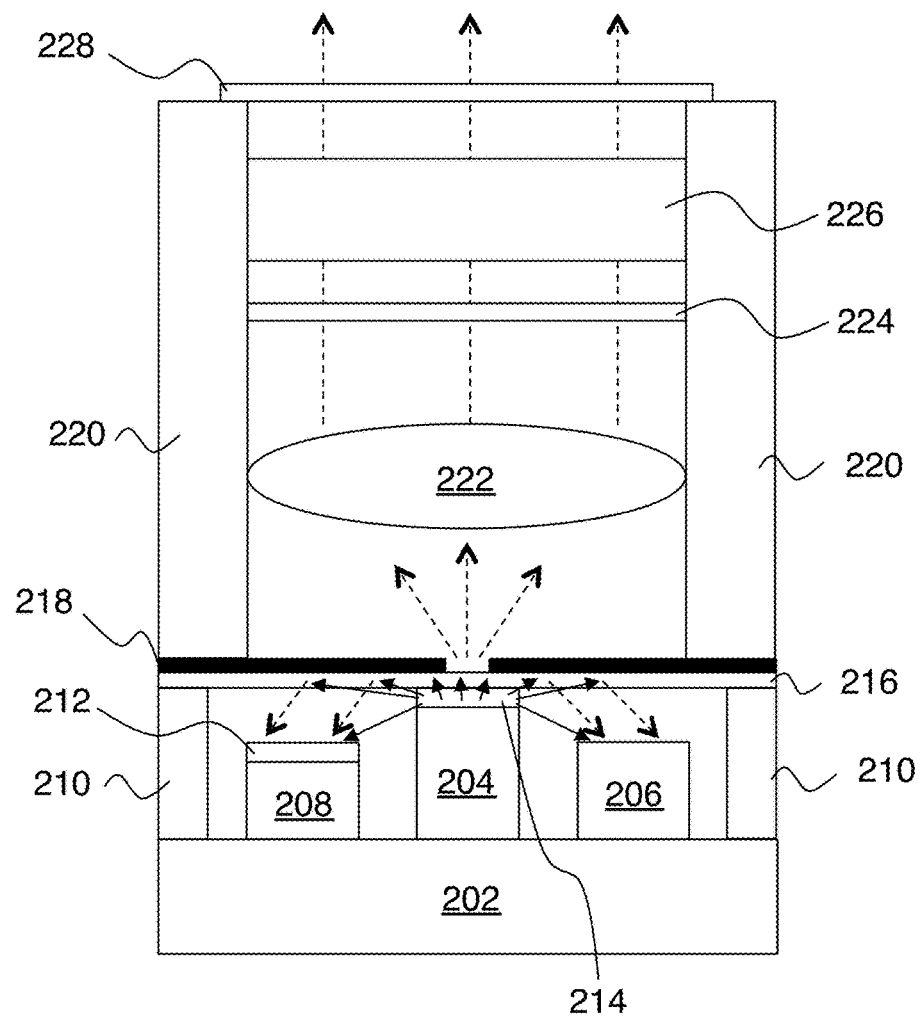
FIG. 2 is a detailed view of an LED source suitable for use in embodiments of the invention.

FIG. 2 is a detailed view of an exemplary LED source suitable for use in embodiments of the invention. In this example of a preferred embodiment, light emitting diode 214 provides LED light (solid arrows), and a phosphor 216 is disposed to receive the LED light and to provide phosphorescence light (dashed arrows). An aperture 218 is configured to provide point source illumination from the phosphorescence light, as shown. A lens 222 is configured to provide collimated light from the point source illumination. Lens 222 is preferably an aspheric lens designed for this collimation function over the wavelength range provided by phosphor 216. A uniformity filter 228 is disposed to receive the collimated light and to provide output light having improved uniformity of illumination.

The example of FIG. 2 also shows further features that are present in preferred embodiments and/or in complete designs. Here LED 214 is mounted on a heat sink member 204, and the package includes a first photodiode 206, a second photodiode 208, and a neutral density filter 212 disposed on the second photodiode. As explained in more detail below, these photodiodes are used in preferred embodiments to provide signals for feedback control of the array of LED light sources. Heat sink 204 and photodiodes 206 and 208 are disposed on substrate 202. Spacer members 210 are used to support the phosphor 216 and aperture 218 at the appropriate vertical height. A lens housing 220 positions lens 222 at the correct distance from aperture 218 to provide collimated (i.e., telecentric) light as shown. Optional components that can be disposed in the path of the collimated light include infra-red (IR) filter 224 and/or diffuser 226. Here the IR filter blocks IR radiation from reaching devices under test to provide purely visible light to the device under test, and the diffuser helps improve the uniformity of light provided by the light source to the device under test.

As shown on FIG. 2 the first photodetector 206 and the second photodetector 208 will typically receive light within the LED light source from both LED 214 (solid arrows) and phosphor 216 (dashed arrows). The phosphor for each LED light source is preferably configured as a thin film of uniform thickness disposed on the light emitting diode of the LED light source, as shown on FIG. 2. Preferably phosphor 216 is a mixture of phosphors chosen to provide substantially white illumination (e.g., by combining red, green and blue emitting phosphors). Alternatively, the phosphor or phosphor mixture can be selected to emphasize a particular desired spectral distribution.

Figure 3:
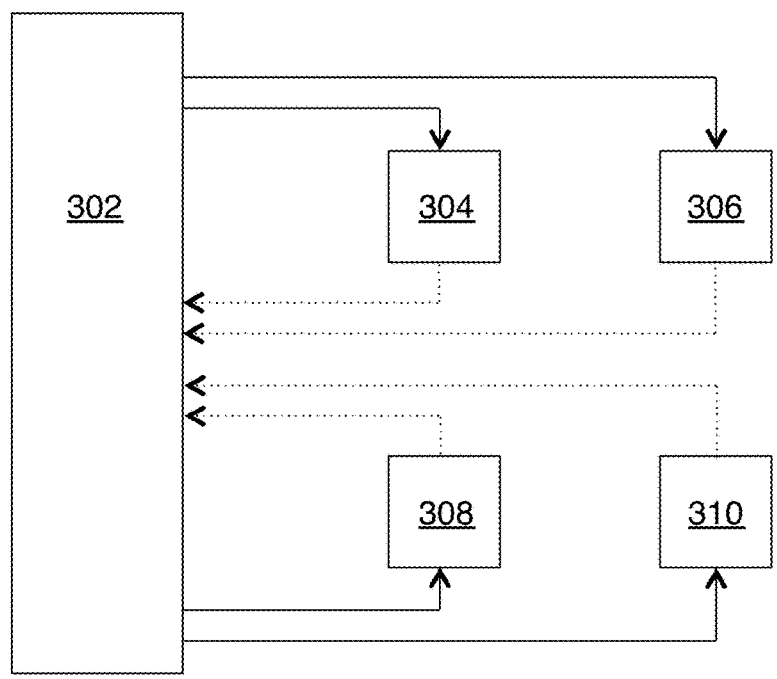
FIG. 3 shows a control approach suitable for use in embodiments of the invention.

An important aspect of preferred embodiments of the invention is feedback control of each LED light source in the emitting array, to provide uniformity of illumination to all devices under test. FIG. 3 shows a control approach suitable for use in embodiments of the invention. Here a feedback control system 302 receives measured optical signals (dotted lines) from each LED light source 304, 306, 308, 310 and is configured to control operation (solid lines) of the array of LED light sources using the measured optical signals to provide uniform illumination to the array of light-sensitive electronic devices. A calibration of the system can be performed to relate measured optical signals to emitted light intensity for each LED light source. This data can then be used to create a lookup table in control system 302 such that each LED light source is driven so that its measured optical signals are in accordance with the lookup table for the desired array intensity. Interpolation in the lookup table can be performed for desired intensity values that are intermediate between calibration data points. Such calibration can be done initially and then repeated occasionally if or as needed to account for drift in device performance over time. For ease of illustration, only four LED light sources are shown in the example of FIG. 3, but such feedback control can be practiced for arrays having any number of LED light sources.

In preferred embodiments like the example of FIG. 2, two feedback signals are used from each LED light source, a first signal from a first photodetector that has no neutral density filter disposed on it, and a second signal from a second photodetector that has a neutral density filter disposed on it. The purpose of having two detectors for feedback configured this way is to improve dynamic range because a single detector can only provide useful feedback over a limited range of optical intensity. So in this example, second detector 208 will be able to provide useful feedback when the optical intensity is high enough to saturate first detector 206 because of neutral density filter 212. Preferably neutral density filter 212 is configured to provide a continuous feedback range for the two detectors combined (e.g., signal from detector 208 is at 1% of its saturation value for the lowest optical intensity that saturates detector 206). Additional feedback detectors plus neutral density filters can be added to further increase dynamic range according to these principles if necessary. Alternatively, a single detector (with or without a neutral density filter on it) can be used to provide the optical signals for feedback.

Uniformity is also improved by making use of uniformity filters 228 in each LED light source. These uniformity filters can be neutral density filters individually customized for their corresponding LED light sources according to calibration measurements of output light uniformity of the array of LED light sources prior to installation of the uniformity filter. In other words, uniformity from one LED light source to another is provided using both active measures (feedback control) and passive measures (the uniformity filters) in combination.

FIGS. 4A-B show first exemplary experimental results for array uniformity. Here FIG. 4A is a table of emission values from an LED array with all drive currents being the same, and FIG. 4B is from the same array after installation of suitable customized uniformity filters for each source in the array. In FIG. 4A, the emission values have a maximum of 555, a minimum of 463, an average of 520 and a standard deviation of 22. In FIG. 4B, the emission values have a maximum of 553, a minimum of 546, an average of 550, and a standard deviation of 1.9. Clearly the array of FIG. 4B provide much more uniform illumination than the array of FIG. 4A, and closed loop control can be expected to further improve illumination uniformity from one LED light source to another.

FIGS. 5A-B show second exemplary experimental results for array uniformity. FIGS. 4A-B are results for one tester type with the apparatus, and FIGS. 5A-B are results for another tester type with the same or similar apparatus. Here FIG. 5A is a table of emission values from an LED array with all drive currents being the same, and FIG. 5B is from the same array after installation of suitable customized uniformity filters for each source in the array. In FIG. 5A, the emission values have a maximum of 551, a minimum of 451, an average of 506 and a standard deviation of 32. In FIG. 5B, the emission values have a maximum of 564, a minimum of 554, an average of 559, and a standard deviation of 2.3. Clearly the array of FIG. 5B provide much more uniform illumination than the array of FIG. 5A, and closed loop control can be expected to further improve illumination uniformity from one LED light source to another.

LED source arrays as in the examples of FIGS. 4A-B and 5A-B have been compared to conventional halogen light sources for testing applications, and the LED source arrays provide comparably uniform illumination to the conventional halogen light sources.

The preceding examples show how uniformity filters can be used to improve uniformity from one device under test to another. It is also possible to use the uniformity filters to improve uniformity of illumination from each LED light source, alternatively to or in addition to improving uniformity between LED light sources.

Figure 6A:
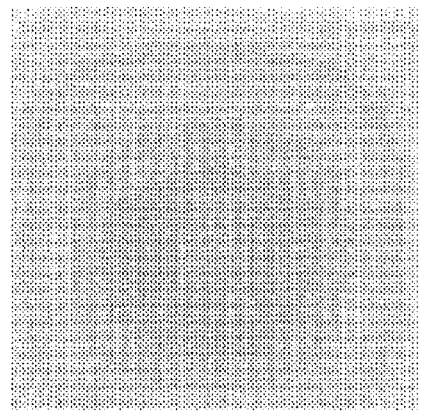
FIGS. 6A-C schematically show how uniformity from a single LED source can be improved.
Figure 6B:
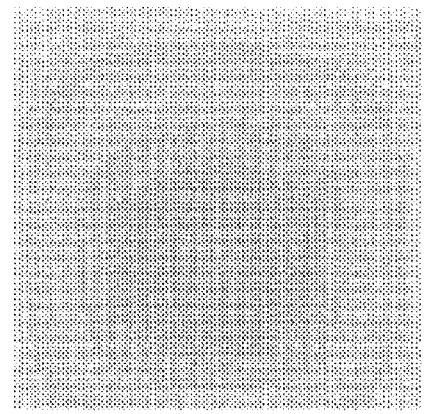
Figure 6C:
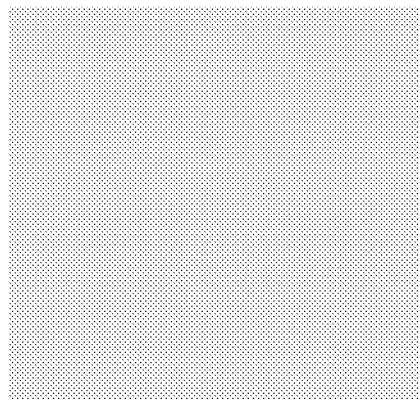

FIGS. 6A-C schematically show how uniformity within a single LED source can be improved. Here FIG. 6A schematically shows a light emission pattern that one might obtain from an LED source as described above. A uniformity filter can be tailored to have transmission as shown on FIG. 6B (i.e., less transmission for the more intense parts of the beam pattern of FIG. 6A, and more transmission for the less intense parts of the beam pattern of FIG. 6A). Photolithography (e.g., chrome on glass or quartz) or the like can be used to make a filter having such variable transmission. Once installed, the resulting intensity distribution should be more uniform, as schematically shown on FIG. 6C. Here the uniformity filter for each LED light source is individually customized for its corresponding LED light source accord-

The invention claimed is:

1. Apparatus for testing an array of light-sensitive electronic devices, the apparatus comprising:
    an array of LED (light emitting diode) light sources, wherein the array of LED light sources is configured to have an LED light source corresponding to each of the electronic devices;
    wherein each LED light source includes a light emitting diode configured to provide LED light;
    wherein each LED light source includes a phosphor disposed to receive the LED light and to provide phosphorescence light;
    wherein each LED light source includes an aperture configured to provide point source illumination from the phosphorescence light;
    wherein each LED light source includes a lens configured to provide collimated light from the point source illumination;
    wherein each LED light source includes a uniformity filter disposed to receive the collimated light and to provide output light having improved uniformity of illumination.

2. The apparatus of claim 1,
    wherein the apparatus is a probe card for testing optoelectronic imaging devices, and
    wherein the probe card further comprises one or more electrical probes for making electrical contact to electrical terminals of optoelectronic imaging devices under test.

3. The apparatus of claim 1, wherein the phosphor for each LED light source is configured as a thin film of uniform thickness disposed on the light emitting diode of the LED light source.

4. The apparatus of claim 1, further comprising:
    a feedback control system configured to measure optical signals from each LED light source and configured to control operation of the array of LED light sources using the measured optical signals to provide uniform illumination to the array of light-sensitive electronic devices.

5. The apparatus of claim 4, wherein the feedback control system is configured to make use of a lookup table derived from calibration measurements of output light from the LED light sources.

6. The apparatus of claim 4, wherein each LED light source further comprises:
    a first photodetector;
    wherein the optical signals are provided by the first photodetector.

7. The apparatus of claim 6, further comprising a neutral density filter disposed on the first photodetector.

8. The apparatus of claim 6, wherein the first photodetector is configured to receive light within the LED light source from both the LED and the phosphor of the LED light source.

9. The apparatus of claim 6, wherein each LED light source further comprises:
    a second photodetector;
    and a neutral density filter disposed on the second photodetector;
    wherein the optical signals are provided by both the first photodetector and the second photodetector.

10. The apparatus of claim 9, wherein the first photodetector and the second photodetector are configured to receive light within the LED light source from both the LED and the phosphor of the LED light source.

11. The apparatus of claim 1, wherein the uniformity filter for each LED light source is individually customized for its corresponding LED light source according to calibration measurements of output light uniformity of its corresponding LED light source prior to installation of the uniformity filter.

12. The apparatus of claim 1, wherein the uniformity filter for each LED light source is individually customized for its corresponding LED light source according to calibration measurements of output light uniformity of the array of LED light sources prior to installation of the uniformity filter.

* * * * *